United States Patent [19]

Marans et al.

[11] 4,049,592
[45] Sept. 20, 1977

[54] BIODEGRADABLE HYDROPHILIC FOAMS AND METHOD

[75] Inventors: Nelson Samuel Marans, Silver Spring; Alan Ricky Pollack, Bethesda, both of Md.

[73] Assignee: W. R. Grace & Co., New York, N.Y.

[21] Appl. No.: 731,295

[22] Filed: Oct. 12, 1976

Related U.S. Application Data

[63] Continuation-in-part of Ser. No. 597,258, July 18, 1975, abandoned.

[51] Int. Cl.² ............................................. C08G 18/14
[52] U.S. Cl. ...................... 260/2.5 AD; 260/2.5 AM; 260/2.5 AN; 260/2.5 AP; 260/2.5 AT
[58] Field of Search ................. 260/2.5 AD, 2.5 AM, 260/2.5 AN, 2.5 AT, 2.5 AP

[56] References Cited

U.S. PATENT DOCUMENTS

| | | | |
|---|---|---|---|
| 3,216,973 | 11/1965 | Britain | 260/2.5 AM |
| 3,451,953 | 6/1969 | Sambeth et al. | 260/2.5 AM |
| 3,778,390 | 12/1973 | Ulrich, Jr. | 260/2.5 AN |
| 3,793,241 | 2/1974 | Kyle et al. | 260/2.5 AM |
| 3,812,619 | 5/1974 | Wood et al. | 260/2.5 AT |
| 3,903,232 | 9/1975 | Wood et al. | 260/2.5 AD |
| 3,905,923 | 9/1975 | Klug | 260/2.5 AD |
| 3,985,688 | 10/1976 | Speech | 260/2.5 AD |

Primary Examiner—Eugene C. Rzucidlo
Attorney, Agent, or Firm—Philip M. Pippenger; William W. McDowell, Jr.

[57] ABSTRACT

The invention disclosed is directed to biodegradable hydrophilic polyurethane structures prepared by using an isocyanate capped hydroxyester polyol reactant with large amounts of aqueous reactant. The resultant foam has economy in handling, and upon contact with liquids or body fluids, the foam is highly absorptive while being readily biodegradable after use.

6 Claims, No Drawings

BIODEGRADABLE HYDROPHILIC FOAMS AND METHOD

CROSS REFERENCE TO RELATED APPLICATION

This is a continuation-in-part of co-pending application Ser. No. 597,258, filed July 18, 1975, and now abandoned.

BACKGROUND OF THE INVENTION

This invention relates to a method for preparing new biodegradable foams. More particularly, the present invention provides new dental and biomedical foams using a hydrophilic polyurethane foam having a biodegradable moiety.

Numerous devices have been proposed in the prior art for use as dental and biomedical foams for absorbing or removing body fluids. Typically, the prior art approaches have relied upon natural materials such as cotton, which is now becoming relatively expensive while providing a resultant structure which is generally fragile in use. Also, the amount of absorption by natural materials is relatively low.

Various polyurethanes have been used as dental and biomedical foams but suffer a disadvantage in that such foams are not readily biodegradable. It has now been found, however, that by practice of the present invention, there is provided a method for preparing new simple and highly efficient dental and biomedical foams which are readily biodegradable after use, and which are characterized by high absorptive ability of body fluids in use.

Various attempts have also been made in the prior art to prepare foams of organic substances for use in cavities of the human body. However, such organic substances typically require, for example, catalysts or the like during the foaming reaction. These additives remain in the foam after foaming and are readily leached into the human body when in contact with body fluids. Thus, although artificial foams, especially those of polyurethane, of the prior art possess the capacity of high absorptivity of body fluids, usage within the human body typically invites disadvantages beyond advantages realized by low cost and high absorptivity. Thus, artificial foams such as polyurethanes of the prior art have received limited practical acceptance by the medical, dental and government regulatory agencies when proposed for internal usage in the human body. There is especially a disadvantage of such foams.

DESCRIPTION OF THE INVENTION

By the present method, new biodegradable foams may be prepared having utility in dental and biomedical applications wherein hydrophilic crosslinked polyurethane foams are employed by reacting a particular isocyanate capped polyhydroxyester polyol with large amounts of an aqueous reactant. The thus generated foams may be formed in handy sizes as desired. Such structures may be readily used in the oral cavity and while in the oral cavity, the structure absorbs oral fluids, and thereafter may be discarded since it is biodegradable.

The novel biodegradable foams are prepared by reacting an isocyanate-capped hydroxyester polyether polyol having a reaction (i.e. isocyanate) functionality of at least 2 with sufficient water to provide an $H_2O$ Index Value (as defined below) of from about 1300 to about 78,000. The polyol is further characterized in that the hydroxyester linkages are formed by condensation of an aliphatic hydroxy carboxylic acid with the hydroxyl groups of a) an essentially linear polyether, or b) a monomeric low molecular weight aliphatic alcohol containing from 3 to 8 hydroxyl groups per mole.

Suitable acids are the monobasic aliphatic carboxylic acids having the structure:

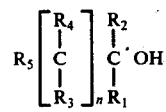

wherein $n$ is an integer and $0 \leq n \leq 20$ and preferably $0 \leq n \leq 5$; $R_1$, $R_2$, $R_3$, $R_4$, and $R_5$ independently are hydrogen, alkyl, alkylene, aryl, aralkyl, alkoxy, carboalkoxy, acyl, acyloxy, and carboxyl with one of the groups $R_1$, $R_2$ or $R_5$ being carboxyl. Suitable alkyl groups can be straight or branched-chain having a total of from 1 to 20 carbon atoms and preferably being a lower aliphatic moiety having from 1 to 5 carbons. The alkylene groups are of the same size as the alkyl groups and contain one or more unsaturated linkages, e.g. olefinic or alkynyl and would include residues from the naturally-occurring fatty acids. Suitable aryl groups are monocyclic and may be substituted with halogen, alkoxy or alkyl groups having less than 4 carbons. Suitable aralkyl groups are benzyl and similar group corresponding to the formula:

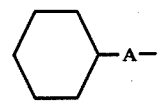

where A is methylene, ethylene, isopropylene, or propylene. Alkoxy groups include both aryloxy (e.g. phenoxy) and lower aliphatic alkoxy groups having from 1 to 5 carbon atoms. Carboalkoxy groups are those of the formula

where B is alkoxy as defined above. Acyl groups are those of the formula

where F is alkyl or alkenyl as defined above, and preferably contains 5 carbons or less. Acyloxy groups are those of formula O-G, where G is acyl as defined above. Hydroxy acids that may be used in this application include but are not limited to glycolic (hydroxy acetic) acid, lactic acid, α-hydroxybutyric acid, α-hydroxyisobutyric acid, α-hydroxyvaleric acid, α-hydroxyisovaleric acid, β-hydroxy propionic acid, β-hydroxy butyric acid, β-hydroxyisobutyric acid, β-hydroxy-n-valeric acid, β-hydroxyisovaleric acid, γ-hydroxybutyric acid, γ-hydroxy-n-valeric acid, δ-hydroxyvaleric acid, ε-hydroxy caproic acid, 9-hydroxystearic acid, 12-hydroxystearic acid, 11-hydroxyhexadecanoic acid, 12-hydroxydodecanoic acid, and 16-hydroxyhexadecanoic acid. Also included are polyhydroxymonocarboxylic acids such as glyceric acid, 3,12-dihydroxypalmitic acid, the erythronic and threonic acids, trihydroxyisobutyric acid, 9,10,16-trihydroxypalmitic acid. Also included are hydroxy unsaturated acids such as α-hydroxyvinylacetic acid, 16-hydroxy-7-hexadecenoic acid, and ricinoleic acid (12-hydroxy-9-octadecenoic acid). From the above description it is apparent that the hydroxy acids are not limited to hydroxyacetic acid but include the straight-chain and omega hydroxy acids having 10 carbons or less.

Suitable aliphatic polyhydroxy alcohols have a molecular weight of less than about 1000 and preferably 500 or less and include glycerol, 1,2,3-butanetriol, 1,2,4-butanetriol, trimethylolethane, trimethylol propane, erythritol, pentaerythritol, adonitol, arabitol, mannitol, sorbitol, iditol, dulcitol, sucrose, dipentaerythritol, triethanolamine and condensation products of ethylene and propylene oxides with ethylene diamine, diethylene triamine, and triethylene tetramine.

The essentially linear polyethers have a molecular weight not exceeding about 4000, and preferably not exceeding about 2000, and are prepared by homopolymerization of ethylene oxide, propylene oxide, and include block copolymers such as polyoxyethylene diol capped with polyoxypropylene chains and polyoxypropylene diols capped with polyoxyethylene. Suitable linear polyethers may also be prepared by condensing an alkylene oxide of 4 carbons or less (e.g. ethylene, propylene or tetramethylene oxide) with a polyhydroxylic alcohol such as those described above. In such condensation products the polyether chains are essentially linear and have an average molecular weight of from 50 up to about 4000. The polyether chains should not contain more than 50% by weight of alkylene oxide condensation units larger than ethylene oxide (e.g. propylene glycol units) and should not contain more than 15% by weight of tetramethylene oxide units.

Suitable isocyanate-capped polyols or prepolymers are exemplified by the following systems:

A. Polyether (e.g. polyoxyethylene glycol) blended with a hydroxyacid ester, e.g. the condensation product of a polyhydroxy alcohol with sufficient hydroxyacid to completely esterify the alcohol. The hydroxyacid ester serves essentially as a crosslinking agent in addition to imparting biodegradability and is employed in amounts sufficient to provide the desired properties, i.e. if it is desired to increase rigidity, solvent resistance and other properties associated with crosslink density, the amount of crosslinking agent is increased. Sufficient isocyanate is added to completely cap all the hydroxyl groups. A specific preferred system is the blend of polyoxyethylene diol with the condensation product of trimethylol propane or ethane with lactic or glycollic acids.

B. Essentially linear polyether completely esterified a polyhydroxy alcohol. Sufficient isocyanate is added to completely cap all the hydroxyl groups.

C. An ester is formed as in A above and the ester is condensed with ethylene or propylene oxides to form essentially linear polyether chains originating with the hydorxyl groups of the ester. Such chains have the molecular weight distribution as described above. Sufficient isocyanate is added to completely cap all the hydroxyl groups. This system may be exemplified by the trimethylol propane (or ethane) ester formed by condensation with lactic acid followed by further condensation of the hydroxyl groups of the ester (3 per mole) with ethylene oxide to provide polyols having three essentially linear polyether chains per mole. Sufficient isocyanate is added to completely cap the hydroxyl groups terminating the polyether chains.

The present foams have utility as handy expandable sponges for personal use. The sponges are easily carried and may be readily prepared with detergents, lotions, perfumes, biostats and the like and upon contact with water, the sponges are found to be very soft, very hydrophilic and biodegradable. The sponges may be used for washing, wiping, cleaning, etc. for external body cleaning; or alternatively for internal body usage such as is necessary in dental and medical applications. The present sponges also have utility as intimate absorptive products, such as diapers, sanitary napkins, incontinent pads and the like.

Polyurethane foam structures prepared herein with hydroxyester polyisocyanates, water and certain surfactants, have an exceptionally fine, uniform, soft, hydrophilic cell structure.

The following conditions seem to be important to obtaining foams of the above-mentioned desirable properties. The polyether (e.g. polyoxyethylene diol) should have a molecular weight not exceeding about 4000. In forming the polyol (prior to capping with isocyanate) for every mole of polyether from about 0.1 to about 4.0 moles, and preferably from about 0.2 to about 2.5 moles of the monomeric aliphatic alcohol should be employed. The necessary hydroxyester linkange is provided by condensing the carboxylic acid with either the hydroxyl groups on the polyether or on the monomeric aliphatic alcohol, as described above. Preferably the carboxylic acid is condensed with the monomeric alcohol to provide a hydroxyester crosslinking agent having from 3 to 8 hydroxyl groups per mole, e.g. trimethylolpropane trilactate, trimethylolethane trilactate or trimethylolpropane triglycolate.

The polyol is next capped with a polyisocyanate (e.g. TDI). The useful range of polyisocyanates is about 0.60 to about 1.3 moles of diisocyanate per equivalent group in the polyol mixture. The preferred range of diisocyanate is about 0.95 to about 1.15 moles of diisocyanate per equivalent of the polyol mixture.

The resultant polyester polyisocyante prepolymers are foamed by reacting with about 10 to about 200 parts of water, preferred range of about 50 to about 160 parts of water, to 100 parts of prepolymer in the presence of about 0.05 to about 30 parts surfactant, preferred range of about 0.1 to about 15 parts surfactant, per 100 parts of prepolymer. The surfactants can be added either to the prepolymer or the water. Surfactants which are soluble in water and/or in their own right are hydrophilic, are preferred.

The polyurethane foams made in the manner described above are exceptionally soft, hydrophilic and biodegradable.

Polyoxyethylene polyol used as a reactant in preparing the capped product to be foamed may have a weight average molecular weight of about 200 to about 4,000, and preferably between about 250 to 3,500, with a hydroxyl functionality of 2 or greater, preferably from about 3 to about 8.

The polyoxyethylene polyol is combined with a crosslinking agent for the prepolymer.

Trimethylolpropane trilactate or the like can be used in combination with other polyols or trimethylolpropane trilactate can be oxyethylated or oxpropylated to yield the appropriate polyol. Other hydroxy acids may be used for the crosslinking agent esterification. These include but are not limited to hydroxyacetic acid and other α, β, γ, Ω, etc., hydroxy acids.

The polyoxyethylene polyol ester mixture is terminated or capped by reaction with a polyisocyanate. The reaction may be carried out according to conventional practice. The polyisocyanates used for capping the polyoxyethylene polyol include polyisocyanates such as PAPI (the brand of polyaryl polyisocyanate manufactured by the Upjohn Co. and defined in U.S. Pat. No. 2,683,730), tolylene diisocyanate, triphenylmethane-4,4′, 4″, -triisocyanate, benzene-1,3,5-triisocyanate, toluene-2,4,6-triisocyanate, diphenyl-2,4,4′-triisoayanate, hexamethylene diisocyanate, xylene diisocyanate, chlorophenylene diisocyanate, diphenylmethane-4,4′-diisocyanate, naphthalene-1, 5-diisocyanate, xylene-alpha, alpha′- diisothiocyanate, 3,3′-dimethyl-4,4′-biphenylene diisocyanate, 2,2′,5,5′-tetramethyl-4,4′-biphenylene diisocyanate, 4,4′-methylenebis (phenylisocyanate), 4,4′-sulfonylbis (phenylisocyanate, 4,4′-methylenebis (orthotolylisocyanate, ethylene diisocyanate, ethylene diisothiocyanate, trimethylenediisocyanate and the like. Mixtures of any one or more of the above-mentioned organic isothiocyanates or isocyanates may be used as desired. The polyisocyanates or mixtures thereof which are espicially suitable are those which are readily commercially available, have a high degree of reactivity and a relatively low cost, e.g. TDI. the aromatic isocyanates are preferred.

Capping of the polyoxyethylene polyol may be effected using stoichiometric amounts of reactants. Desirably, however, an excess of isocyanate is used to insure complete capping of the polyol. Thus, the ratio of isocyanate groups to the hydroxyl groups used for capping is between about 1 to about 4 isocyanate to hydroxyl, and preferably about 2 to about 3 isocyanate to hydroxyl molar ratio. In order to achieve an infinite crosslinked network formation on foaming, the reactive components may be formulated in one of the following by way of example. First, when water is the sole reactant with the isocyanate groups leading to chain growth during the foaming process, the isocyanate-capped reaction product must have an average isocyanate functionality greater than 2 and up to about 6 or more depending upon the composition of the polyol and capping agent components. Secondly, when the isocyanate capped reaction product has an isocyanate functionality of only about two, then the aqueous reactant, may contain a dissolved or dispersed isocyanate-reactive crosslinking agent having an effective functionality greater than two. In this case, the reactive crosslinking agent is reacted with the capped resin when admixed during and after the foaming process has been initiated. Thirdly, when the isocyanate capped resin has an isocyanate functionality of only about two, then a polyisocyanate crosslinking agent having an isocyanate functionality greater than two may be incorporated therein, either preformed or formed in situ, and the resultant mixture may then be reacted with the aqueous reactant, optionally containing dissolved or dispersed reactive isocyanate-reactive crosslinking agent, leading to a crosslinked, infinite network hydrophilic polyurethane foam.

Water soluble or water dispersible crosslinking agents operable in this invention desirably should be polyfunctional and reactive with isocyanate groups and include but are not limited to materials such as diethylenetriamine, triethylenetetramine, tetraethylenepentamine, polyethyleneimine, glycerol, trimethylolpropane, pentaerythritol, tolylene-2,4,6-triamine, ethylenediamine, aminoethanol, trimethylenediamine, tetramethylenediamine, pentamethylenediamine, hexamethylenediamine, ethanolamine, diethanolamine, hydrazine, triethanolamine, benzene-1,2,4-tricarboxylic acid, nitrilotriacetic acid, citric acid, 4,4′-methylenebis (o-chloroaniline), and the like. The water soluble or water dispersible crosslinking agents chosen are those which cause a crosslinked network to form during or after the foaming process begins to take place.

It has also been found that the capped resin having an isocyanate functionality greater than two used to prepare a three dimensional network polymer must be present in an amount sufficient to insure formation of the dimensional network. Thus, amounts of the capped polyoxyethylene polyol having an isocyanate functionality greater than 2 in the component to be foamed range from about 3% by weight of this component up to 100% by weight. Thus, it is possible to include a capped polyoxyethylene polyol having a terminal member with an isocyanate functionality of two i.e., a diisocyanate in an amount from 0% by weight up to about 97% by weight of the component to be foamed. The maximum amounts of diisocyanate used are limited to that necessary to permit crosslinking to take place during foaming, as contrasted to formation of a linear polymeric structure, and the properties desired in the finally prepared foam.

To effect foaming and preparation of the crosslinked network polymer, the component including the isocyanate capped polyoxyethylene polyol having a functionality about 2 or greater is simply combined with the aqueous component. For simplicity, this isocyanate capped reaction component will herein be referred to as resin reactant.

The aqueous component, i.e., water slurry or suspension, may include various additives such as detergents, biostats, perfumes or the like as desired for use in a given product. Obviously, additives are avoided or carefully selected for specific purposes for foam structures intended for internal body usage.

The dramatic way in which additions of water influences practice of the present invention is by consideration of the following water index value;

$$\text{Water Index value} = \frac{\text{equivalents of } H_2O}{\text{equivalents of NCO}} \times 100$$

Thus, because one-half mole of water is equal to one equivalent of isocyanate, where 0.5 m $H_2O$ is used with 1 eq. NCO, the water index value is 100.

An Index of 100 indicates that both equivalents are equal or "balanced". An Index of 95 indicates that there is a 5% shortage of water while an Index of 105 indicates a 5% surplus of water. A slight theoretical excess of isocyanate, usually 3–5%, is common practice, in the prior art particularly with flexible foams.

using the present resin reactant and water in amounts from about $H_2O$ Index Value of 100 up to about $H_2O$ Index Value of 200, poor foaming results unless materials such as surfactants or the like are included. Amounts up to about $H_2O$ Index Value of 200 require a catalyst. When using about $H_2O$ Index Value 78,000, surprisingly good foams result which improve in characteristics with added amounts of molar water. Thus, the available water content in the aqueous reactant is from about an $H_2O$ Index Value of about 1300 to about 78,000 and desirably from about 4,000 to about 40,000.

"Available water" in the aqueous reactant is that water accessible for reaction with the resin reactant, and which is exclusive of water which may layer during reaction, or supplemental water which may be necessary because of additives present in the forming the aqueous reactant.

Because large amounts of water are in the aqueous reactant during reaction, i.e., the present system is not dependent upon a molar NCO-water type reaction, it is possible to combine a great variety of materials in the aqueous reactant which are otherwise not possible with limited water reacting systems.

The aqueous reactant may be used at temperatures from about 2° C. to about 100° C. as desired.

Although foaming of the present resin reactant, i.e., prepolymer, is effected simply, it is also possible to add, although not necessary, supplemental foaming materials such as those well known to the artificial sponge foaming art.

After foaming has been effected, the foam may be dried, if desired, under vacuum from 1 to 760 Torr at a temperature of about 0° to about 150° C. When used internally, the foams may be heat or chemically sterilized prior to use.

The following examples will aid in explaining, but should not be deemed as limiting, practice of the present invention. In all cases, unless otherwise noted, all parts and percentages are by weight.

EXAMPLE 1

Polyethyleneglycol PEG 1000 (actual M.W. 1064) and trimethylolpropane trilactate (361g and 60g respectively) were dried for 2.5 hours at 103° C. and 4 Torr. This mixture was added to 225g of toluenediisocyanate and 0.2g of Metal and Thermit T-9 catalyst, a catalyst containing stannous octoate, over a period of 80 minutes at a temperature of 60° C. After completion of addition, the reaction mixture was maintained at 60° C. for an additional hour. To the reaction mixture there was then added an additional 12g of tolylenediisocyanate and heating continued for another hour at 60° C. The final viscosity was 24,500 cp at 25° C. and the NCO was 2.38 meq/g (theory 2.33 meq/g).

From the above reaction mixture, a foam was prepared using 100 g of prepolymer, 10g of Union Carbide Silicone surfactant L-520 and 100 g of water. Aqueous solutions of enzymes, 1%, were prepared and tested on this foam. Maxatase, H.T. proteolytic concentrate, and protease amylase, gave essentially complete degradation after seven days at 25° C. Several others, such as mucinase, trypsin and some experimental enzyme broths, showed some evidence of degradation. A standard polyurethane foam prepared from 100 pts of prepolymer, isocyanate capped polyoxyethylene polyol, 1 pt 1-520 and 100 pts of water gave no change over the same period of time with these enzymes.

The foam was buried in a compost heap for three months. On removal from the compost heap, the foam had started to fragment and could not be washed without falling apart.

The foam was then compared with a foam made in a similar manner with trimethylolpropane instead of the trimethylolpropane trilactate. The trimethylolpropane lactate based foam in ten minutes at 250° F. turned tacky and began to degrade. The trimethylolpropane based foam showed no change in 20 minutes at 250° F. Conventional polyoxypropylene based polyurethanes shown no change in three hours.

A similar comparison at 100° C. in boiling water gave breakdown into viscous lumps in 240 minutes after becoming tacky in 30 minutes for the trimethylolpropane trilactate biodegradable polymeric foam. The trimethylolpropane based foam showed no change in 240 minutes at 100° C.

EXAMPLE 2

The procedure of Example 1 was repeated for foam generation. Next a synthetic sewage sludge was allowed to react with the foam for one week. The trimethylolpropane trilactate based foam had completely disintegrated. The standard polyurethane foam was intact.

EXAMPLE 3

The trimethylolpropane trilactate that had been prepared was used with a different polyol. A mixture of one mole each of trimethylolpropane trilactate and Pluronic 10-R-5 (a Wyandotte polyol with a molecular weight of 1970, an equivalent weight of 985 and end-capped with oxypropylene on an oxyethylene backbone with approximately 50% by weight of oxypropylene and 50% by weight of oxyethylene) was dried at 110° C. and 3 torr for three hours. The mixture was then added to 4.75 moles of the standard 80-20 mixture of 2,4 and 2,6-tolylenediisocyanate over a period of 1 hour maintaining the temperature at 60° C. The reaction was completed by heating for an additional three hours at 60° C. with the addition of Metal and Thermits' T-9 stannous octoate catalyst (5 drops). To the final prepolymer was added 0.75 moles of tolylenediisocyanate to give a prepolymer with a viscosity of 17,250 cp. The prepolymer was converted to a foam by the additon of 1 part of silicone surfactant L-520 to the prepolymer (100 parts) and then adding 100 parts water to the prepolymer phase. The polymeric foam when placed in a synthetic sewer sludge disintegrated within one week.

EXAMPLE 4

The trimethylolpropane trilactate was prepared as above in Example 3. A mixture was prepared from one mole of timethylolpropane lactate and 0.5 mole Pluronic P-65 supplied by Wyandotte (this polyol has a molecular weight of 3500 and has a polyoxypropylene base, end-capped with oxyethylene units, being 50% oxyethylene and 50% oxypropylene by weight) and was dried by heating for a period of 3 hours at 115° C. and 5 torr. This mixture was added to 3.8 moles of commercial TDI over a period of 1 hour with the temperature maintained at 60° C. After completion of the addition, 10 drops of Metal and Thermit catalyst T-9 was added and the reaction mixture was heated for an additional 3 hours at 65° C. to force the prepolymer formation. Then 0.6 mole of TDI was added to the reaction mixture and the reaction heated for an additional 2 hours to give a prepolymer with a viscosity of 16,000 cp at 25° C. A foam was prepared from this prepolymer using 100 parts of prepolymer, 1.0 part of Plurafac B-26, 1.7 parts a tertiary amine of Thancat DD catalyst by Jefferson Chemicals, and 50 parts of water (the latter three all being in the aqueous phase). The foam that was formed decomposed in a compost heap in two months. The conventional polyoxypropylene polyurethane foam showed no change.

EXAMPLE 5

Trimethylolpropane hydroxyacetate (glycolate) is prepared by simple esterification using one mole trimethylolpropane and 3.12 moles glycolic acid (hydroxyacetic acid). the mixture was heated for four hours at reflux and then stripped at 125° C. and 12 Torr.

The prepolymer was prepared by adding a dried mixture of 2.0 moles of PEG-1000 (molecular weight 1064) and 1.0 mole of trimethylolpropane triglycolate to 6.7 moles of tolylenediisocyanate over a period of one hour at a reaction flask temperature of 60° C. The reaction was continued at 60° C. for an additional 3 hours and the measured NCO content in meq/g. was 1.82 meq/g(theory 1.78 meq/g.). To the reaction mixture was then added an additional 1.0 mole of TDI with heating and stirring continued for an additional two hours at 60° C. The NCO was 2.18 meq/g(theory 2.23 meq/g.), viscosity at 25° C. 19,000 cp.

A foam was prepared from this prepolymer by using 100 g. of prepolymer and 100 parts of 5% solution of Plurafac B-26 (By Wyandotte) in water. The generated foam was found to degrade with Mexatase enzyme in six days at 25° C. while the foam prepared from trimethylolpropane was intact. In boiling water, decomposition occurred in 200 minutes with the trimethylolpropane glycolate based material. With the trimethylolpropane based prepolymer, no change was noted in the same time period.

EXAMPLE 6

Instead of preparing the hydroxyacid ester of the crosslinking agent as in the previous example, the hydroxyacid ester of polyoxyalkylene glycol was prepared. To 1 mole of polyethylene glycol having a molecular weight of 1064 (PEG-1000) there was added 2.22 moles of 88% lactic acid. The mixture was refluxed for 4 hours after which the residual lactic acid was stripped at 130° C. and 4 Torr.

The product weighing 1215 g., mainly polyethylene glycol dilactate, was combined with 67 g. of trimethylolpropane and stripped of residual water at 105° C. and 3 Torr for four hours. This mixture was then added at 60° C. flask temperature to 574 g. of tolylenediisocyanate over a period of 2 hours. The reaction mixture was then heated for an additional 4 hours at 60° C. To the reaction mixture was then added an additional 87 g. of tolylenediisocyanate in thirty minutes at 60° C. and the reaction mixture heated for an additional two hours at 60° C. The NCO content was 2.06 meq/g.(theory 2.11 meq/g.); the viscosity was 18,000 cp at 25° C.

A foam was prepared from the prepolymer of this example using 100 parts of prepolymer and 100 parts of 5% solution of Pluronic P-75 in water. The final foam was dried and on treatment with a synthetic sewer sludge, disintegrated within ten days. A similar sample was prepared from a prepolymer containing polyethylene glycol 1000 and trimethylolpropane showed no signs of decomposition in the same period of time.

It is understood that the foregoing detailed description is given merely by way of illustration and that many variations may be made therein without departing from the spirit of this invention.

What is claimed is:

1. A method of preparing biodegradable foam structures having three-dimensional networks, said method comprising, foaming a first component comprising isocyanate capped hydroxyester polyol having a reaction functionality of at least 2 with a second component comprising aqueous reactant wherein the $H_2O$ Index Value is about 1,300 to 78,000, the hydroxyester linkages in said polyol formed by condensation of an aliphatic hydroxy carboxylic acid with the hydroxyl groups of (a) an essentially linear polyether, or (b) a monomeric low molecular weight aliphatic alcohol containing from 3 to 8 hydroxyl groups per mole.

2. The method of claim 1 wherein the isocyanate capped hydroxyester polyol is present in the first component in an amount from about 3% by weight up to 100% by weight, wherein an isocyanate capped polyoxyethylene polyol having a terminal member with an isocyanate functionality of two is present in an amount from 0% up to about 97% by weight.

3. The method of claim 1 wherein the polyol moiety of the isocyanate capped member has a weight average molecular weight of about 200 to about 20,000, and a hydroxyl functionality of about 2 to about 8.

4. The method of claim 3 wherein the weight average molecular weight is about 250 to about 6,000.

5. The method of claim 3 wherein the $H_2O$ Index Value is from about 4,000 to about 40,000.

6. The product prepared by the method of claim 1.

* * * * *